(12) United States Patent
Tararov et al.

(10) Patent No.: US 8,148,550 B2
(45) Date of Patent: Apr. 3, 2012

(54) METHOD FOR THE PRODUCTION OF STATINS

(75) Inventors: Vitali Tararov, Moscow (RU); Armin Boerner, Rostock (DE); Gerd Koenig, Zwickau (DE); Andrei Korostylev, Ryazan (RU)

(73) Assignee: Ratiopharm GmbH, Ulm (DE)

( * ) Notice: Subject to any disclaimer, the term of this patent is extended or adjusted under 35 U.S.C. 154(b) by 977 days.

(21) Appl. No.: 11/914,317

(22) PCT Filed: Apr. 28, 2006

(86) PCT No.: PCT/EP2006/003987
§ 371 (c)(1), (2), (4) Date: Jan. 22, 2008

(87) PCT Pub. No.: WO2006/122644
PCT Pub. Date: Nov. 23, 2006

(65) Prior Publication Data
US 2008/0249306 A1    Oct. 9, 2008

(30) Foreign Application Priority Data
May 13, 2005  (DE) .................. 10 2005 022 284

(51) Int. Cl.
*C07D 323/02* (2006.01)
*C07D 309/12* (2006.01)
*C07F 7/18* (2006.01)

(52) U.S. Cl. ........ 549/214; 548/492; 548/494; 548/517; 546/282.1; 544/332

(58) Field of Classification Search .................... 549/214
See application file for complete search history.

(56) References Cited

FOREIGN PATENT DOCUMENTS

| EP | 0 583 171 A2 | 2/1994 |
|---|---|---|
| WO | WO 2004/096788 | 11/2004 |
| WO | WO 2005/012246 | 2/2005 |

OTHER PUBLICATIONS

Beck G et al., J. Med. Chem., vol. 33(1): 52-60 (1990).
Claffey Michelle et al., J. Org. Chem., vol. 64 (2): 8267-8274 (1999).
Ghosh Arun et al., J. Org. Chem., vol. 67: 8783-8788 (2002).
Rosen Terry et al., JACS, vol. 49 (21): 3994-4003 (1984).
Smith Amos et al., JACS, vol. 119 (45): 10935-10946 (1997).
Tavares Francis et al., JACS, vol. 118 (13): 3303-3304 (1996).
Yang YL et al., Tetrahedron Ltrs., vol. 23 (42): 4305-4308 (1982).
Written Opinion of the International Searching Authority for PCT/EP06/003987 (PCT/ISA/237), (2007).

*Primary Examiner* — Bernard Dentz
(74) *Attorney, Agent, or Firm* — Kenyon & Kenyon LLP

(57) ABSTRACT

The present invention relates to a process for the production of statins, which are known as HMG-CoA reductase inhibitors. A few of the intermediate compounds for use in the process in accordance with the invention are novel compounds and the invention also relates to these novel intermediate compounds.

25 Claims, No Drawings

METHOD FOR THE PRODUCTION OF STATINS

This application corresponds to the national phase of PCT Application No. PCT/EP06/003987, filed Apr. 28, 2006, which, in turn, claims priority to German Patent Application No. 10 2005 022 284.6, filed May 13, 2005, the contents of which are incorporated by reference herein in its entirety.

The present invention relates to a process for the production of statins, which are HMG-CoA reductase inhibitors. A few of the intermediate compounds for use in the process in accordance with the invention are novel compounds and therefore the invention also relates to these novel intermediate compounds.

Statins are a known class of active substances that inhibit the enzyme hydroxymethylglutaryl(HMG)-CoA-reductase. These active substances are widespread, especially as anticholesteremics in the blood. Known statins are, for example, cerivastatin, fluvastatin, itavastatin, BMY22089, rosuvastatin, glenvastatin and atorvastatin. Synthesis paths for producing statins are known and have been described in several publications. Statins generally comprise an aromatic, heterocyclic or an aromatic-heterocyclic, substituted or non-substituted, mono-, di- or polycyclic ring system on which the so-called statin side chain, either in the open-chain form or in the lactone form, is attached as shown in the formula below:

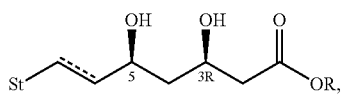

wherein St represents the previously described ring system, i.e. the statin group. As used herein, the term "statin" also includes pharmaceutically acceptable salts, hydrates, solvates, esters and ethers of the statins described in the art.

The spatial arrangement of the hydroxyl groups of the statin side chain, as shown in the above formula, is of decisive significance for the effectiveness of the statins. It is economically desirable when synthezing statins to determine the stereochemistry at a very early stage and to carry out the further chemical steps while preserving the stereochemistry, and thus the stereoselectively of the resulting statin, in order to obtain the highest possible yields of the final product (products with another stereochemistry must be separated out).

Processes for the production of statins have long been known, but are still an object of chemical research. The following reaction is described, among other things, in an early publication in 1984 (J. Org. Chem. vol. 49, No. 21, 1984, 3994-4003, which is incorporated herein by reference.)

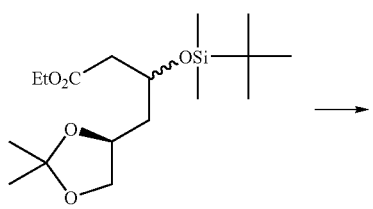

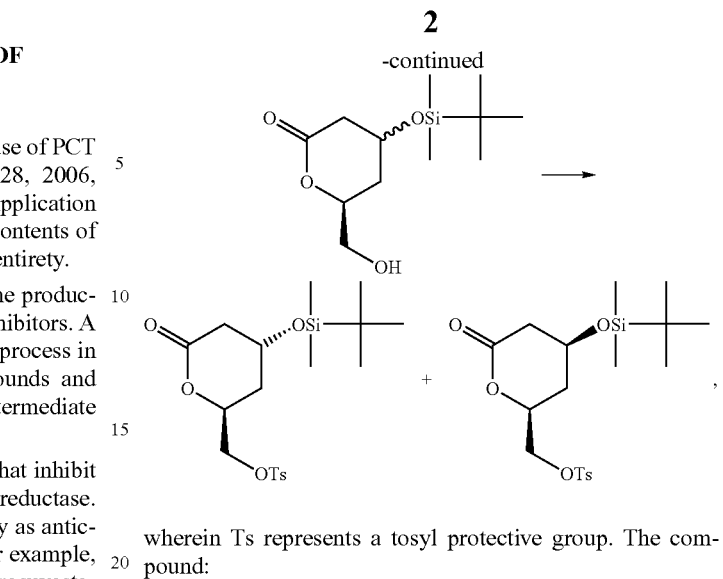

wherein Ts represents a tosyl protective group. The compound:

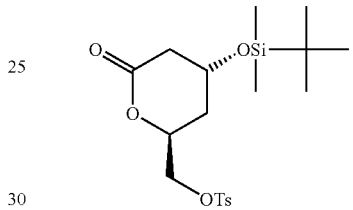

is considered as a possible intermediate product for the production of the lactone group of compactin, one of the first statins. However, the publication assumes that, in order to isolate this compound, resolution of the racemate:

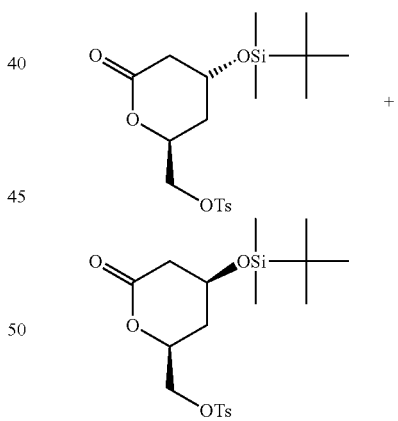

is necessary, which makes the entire process ineffective.

Other synthetic paths for producing modern statins, which do not involve this silylated intermediate compound, were also disclosed in the art. An alcohol whose hydroxyl groups are protected in the 5 and 6 position by a bridging protecting group, like the initial compound of the previous synthesis, was used, occasionally only and with moderate success in the synthesis of statins. See, for example, EP-A 374 922, which is incorporated herein by reference and discloses the production of 5,6-O-isopropyliden-3,5,6-trihydroxyhexanoic acid ethylester. The end product of this synthesis contained the desired (3R,5S) isomer, but only in a ratio of 78:22, which is not satisfactory for commercial purposes. A reaction of this compound to yield a lactone did not take place.

More recent processes for the synthesis of statins, as described for example in EP-A 583 171, which is incorporated herein by reference, take place, in contrast to the above, via intermediate compounds in which the hydroxyl protective groups in the 3 and 5 position of the trihydroxyhexanate are protected by a bridging protective group. Also, other processes do not take place via a lactonization reaction and proceed via intermediate compounds in which bridging protective groups are completely eliminated.

Typical examples illustrating the direction in which the art is moving in statin synthesis can be found in WO 03/004450 and WO 03/004456, which are incorporated herein by reference. These publications disclose so-called "key intermediate products":

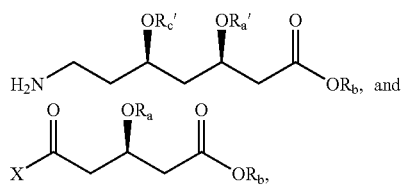

that can be coupled, after further reactions, to the statin group. These "key intermediate products" are produced by saponification of a racemic mixture of the compound:

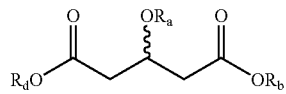

using an enantioselective catalyst.

This process has the advantage that the stereochemistry of the statin side chain is fixed at an early stage. However, this process is quite complex. Also, the stereoselective hydrolysis of the compound:

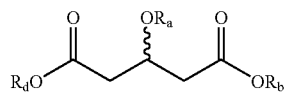

is associated with yield loss and there is a risk that the stereochemistry of the side chain will be lost in the process.

There is therefore a significant need for processes for producing statins that are economical and that allow producing statins with high yields and using fewer process steps.

As explained above, the early experiments, such as that described in J. Org. Chem., vol. 49, No. 21, 1984, 3994-4003 for example, were up to now considered as not very promising. It was found in accordance with the present invention that a statin synthesis along the lines of these early experiments provides statins with the desired statin side chain in a good yield and with high optical purity if the synthesis takes place via a lactol intermediate step. A few of the intermediate products involved in this new synthesis are known in the literature, while others are novel compounds. According to the invention, a process was also found in which these intermediate products can be readily produced with a high yield.

The invention therefore relates to a process for the production of a statin comprising the following step:
a) reduction of a compound of formula II:

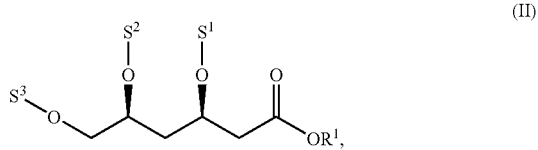

wherein
$S^1$ is a hydrogen atom or a hydroxyl protective group,
$S^2$ and $S^3$ are, independently of one another, hydroxyl protective groups, and wherein $S^2$ and $S^3$ together can be a bridging hydroxyl protective group, and
$R^1$ is a hydrogen atom or a carboxyl protective group,
to yield a compound of formula VI:

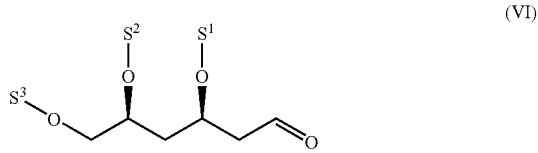

wherein $S^1$, $S^2$ and $S^3$ are as defined above,
or
b) lactonization of a compound of formula II:

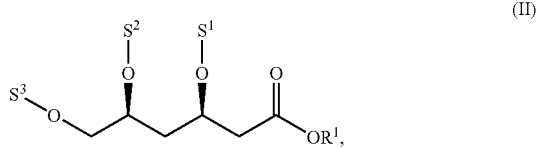

wherein $S^1$, $S^2$, $S^3$ and $R^1$ are as defined above, and subsequent reduction of the lactone to yield a compound of formula I-a:

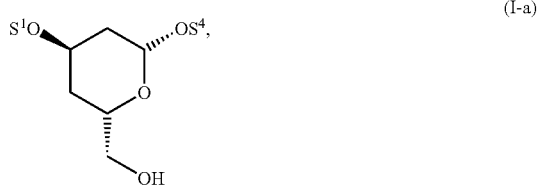

wherein $S^1$ is as defined above and $S^4$ is a hydrogen atom or a hydroxyl protective group.

The reduction can take place, for example, under cooling (for example −78° C.) in ethanol by means of DIBALH (diisobutylaluminum hydride).

$S^1$ is a hydrogen atom or a hydroxyl protective group. Hydroxyl protective groups are known in the art, and reference can be made, for example, to general literature such as Protective Groups in Organic Synthesis, Theodora W. Greene and Peter G. M. Wuts, 2nd edition, John Wiley & Sons. Suitable hydroxyl protective groups are also cited, for example, in WO 03/004450, which is incorporated herein by reference. According to the invention, hydroxyl protective groups with 4 to 10 carbon atoms and optionally 1 to 3 heteroatoms are preferred. The hydroxyl protective group especially preferably contains a silicon atom, 5 to 10 carbon atoms and no further heteroatoms. The hydroxyl protective group $S^1$ is especially preferably a trimethylsilyl, triisopropylsilyl, triethylsilyl, tert-butyldimethylsilyl, di-tert-butylmethylsilyl, tert-butyldiphenylsilyl, triphenylsilyl, diphenylmethylsilyl or tris(trimethylsilyl)silyl protective group. The hydroxyl protective group $S^1$ is most preferably a tert-butyldiphenylsilyl group. Protective groups of the general formula R—O—C(O)— and R—C(O)—, wherein R is an alkyl group, especially a $C_1$-$C_6$ alkyl group, such as a tert-butyl group, or an aryl group, especially a $C_5$-$C_{10}$ aryl group, such as a phenyl group, or an alkyl-aryl group, especially a $C_1$-$C_6$ alkyl-$C_5$-$C_{10}$ aryl group, are also preferred.

$S^2$ and $S^3$ can be customary hydroxyl protective groups. The hydroxyl protective groups mentioned above with respect to $S^1$ can be used. Again, the standard work Protective Groups in Organic Synthesis, Theodora W. Greene and Peter G. M. Wuts, 2nd edition, John Wiley & Sons can be referred to. However, $S^2$ and $S^3$ together can also form a bridging hydroxyl protective group as generally known. Examples of suitable bridging hydroxyl protective groups are disclosed in WO 03/004450, which is incorporated herein by reference. Preferably, $S^2$ and $S^3$ together form an isopropylidene protective group.

$R^1$ is a hydrogen atom or a carboxyl protective group. Carboxyl protective groups are known to the person of ordinary skill in the art and are described, for example, in Protective Groups in Organic Synthesis, Theodora W. Greene and Peter G. M. Wuts, 2nd edition, John Wiley & Sons. $R^1$ can be, for example, a hydrogen atom, a $C_{1-3}$ alkyl or $C_{5-10}$ aryl group. The $C_{1-3}$ alkyl and $C_{5-10}$ aryl groups may optionally be substituted with one or more groups independently selected from halogen atoms, $C_1$-$C_{10}$ alkyl groups, $C_5$-$C_{10}$ alkoxy groups, heterocycles comprising from 0 to 10 carbon atoms, preferably 1 to 5 carbon atoms, and 1 to 10 heteroatoms, preferably 1 to 5 heteroatoms, selected from sulfur, nitrogen and oxygen atoms, and functional groups. Preferably, $R^1$ is a $C_{1-8}$ alkyl or $C_{5-10}$ aryl optionally substituted with one or more groups independently selected from halogen atoms, tetrazolyl, $C_{1-8}$ alkyl, $C_{1-8}$ alkoxy, nitro and cyano.

Especially preferably, $R^1$ is a $C_{1-8}$ alkyl group, more preferably a $C_{1-8}$ alkyl group, and most preferably an ethyl group, especially when $S^1$ is a tert-butyldiphenylsilyl group.

The compound of formula VI can readily be converted into a lactol of formula I-a, which is the desired intermediate product for the synthesis of statins:

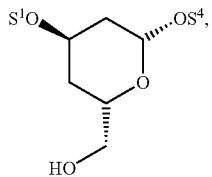
(I-a)

wherein $S^4$ is a hydrogen atom or a hydroxyl protective group as previously defined for $S^1$.

The compound of formula I-a:

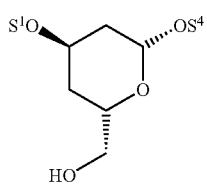
(I-a)

can readily be converted into compounds of formula I:

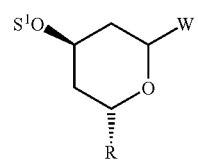
(I)

that also are intermediate compounds in the production of statins.

In compounds of formula I:

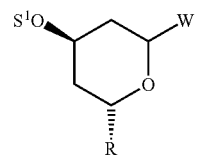
(I)

$S^1$ is as previously defined. W is =O or $OS^4$. R is a group via which the compound of formula I can be coupled to the statin group, especially —$CH_2R^2$, —CHO, —CH=P($R^3$)$_3$,

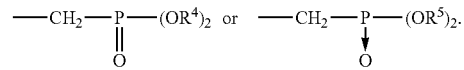

The group —CH=P($R^3$)$_3$ is present in equilibrium with the group —$^-$CH—$^+$P($R^3$)$_3$. Therefore, as a result, —$CH_2$—$P^+$($R^3$)$_3M^-$ groups, wherein $M^-$ is a customary counterion, for example, $Hal^-$ (Hal=Cl, Br or I) or $^-$O-Tos are also included.

If the R group is —CH=P($R^3$)$_3$,

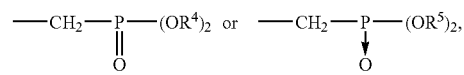

the compound of formula I is a Wittig reagent or a Horner-Wittig reagent that can perform a Wittig reaction or a Horner-Wittig reaction with the appropriately functionalized ring system St of the statin. In this case, the ring system St of the statin with which the compound of formula I is reacted should preferably carry an aldehyde group on the coupling site.

$R^3$, $R^4$ and $R^5$ are preferably the customary groups that complete a Wittig group or a Horner-Wittig group so that the compounds can perform a Wittig reaction or a Horner-Wittig reaction. $R^3$ may be a $C_5$-$C_{10}$ aryl group that can be optionally substituted with one or two $C_1$-$C_4$ alkyl groups and/or halogen atoms, a $C_1$-$C_4$ alkyl group or a $C_5$-$C_{10}$ cycloalkyl group. Especially, $R^3$ may be a phenyl group, a n-$C_1$-$C_4$ alkyl group or a cyclohexyl group. The phenyl group is preferably non-substituted. The phenyl group is also preferably substituted with one or two n-$C_1$-$C_4$ alkyl groups or chlorine atoms. $R^4$ is preferably a $C_1$-$C_4$ alkyl group, especially a n-$C_1$-$C_4$ alkyl group, especially preferably an ethyl group. $R^5$ is preferably a $C_5$-$C_{10}$ aryl group or a $C_1$-$C_6$ alkyl group, especially a $C_5$-$C_{10}$ aryl group or a $C_1$-$C_4$ alkyl group, especially preferably a phenyl, methyl or ethyl group. However, these groups are not especially limited in so far as the later required Wittig (or Horner-Wittig) reaction can be carried out with them.

If R in the compound of formula I is an aldehyde group, the ring system St, with which the compound of formula I is reacted to the corresponding statin, should have a corresponding functional group so that a Wittig reaction or a Horner-Wittig reaction can be carried out.

Wittig and Horner-Wittig reactions are known conversion reactions and pertinent textbooks of organic chemistry can be referred to. See for example March, Advanced Organic chemistry, 4th edition, 1992, John Wiley and Sons.

If R is a —$CH_2R^2$ group, according to the invention $R^2$ is a halogen atom, in particular chlorine, bromine or iodine, cyanide (—C≡N), —$CH_2NH_2$, $SO_2$—$R^6$ or a leaving group.

If $R^2$ is a cyanide group, the compound of formula I is, in particular, an intermediate product for producing a compound of formula I wherein $R^2$ is —$CH_2NH_2$. The compound of formula I wherein $R^2$ is —$CH_2NH_2$ is an especially preferred intermediate product suitable for producing atorvastatin.

A compound of formula I wherein $R^2$ is cyanide can be converted by hydrogenation into a compound of formula I wherein $R^2$ is —$CH_2NH_2$.

The compounds of formula I wherein $R^2$ is —$SO_2R^6$ can be converted into a statin by reaction with a ring system St carrying, for example, an aldehyde group as coupling group, as described above with regard to the compounds wherein R is a Wittig group or a Horner-Wittig group. The corresponding sulphones can be obtained either directly from the alcohols of formula I-a or from the tosylates of formula I, for example, by reacting with sulfides and subsequent oxidation with peroxides or $H_2O_2$, as described in, for example, Tetrahedron Letters, 1973, 49, 4833-4836; Synlett 1988, 26-28 or J. Am. Chem. Soc. 2001, 123, 10772-10773.

$R^6$ is a hydrogen atom, a $C_{1-3}$ alkyl or $C_{5-10}$ aryl group, the $C_{1-3}$ alkyl or $C_{5-10}$ aryl groups being optionally substituted with one or more groups independently selected from halogen atoms, $C_1$-$C_{10}$ alkyl groups, $C_1$-$C_{10}$ alkoxy groups, heterocycles made up of from 0 to 10 carbon atoms, preferably 1 to 5 carbon atoms, and 1 to 10 heteroatoms, preferably 1 to 5 heteroatoms, selected from sulfur, nitrogen and oxygen atoms, and functional groups. $R^6$ is preferably a hydrogen atom, a $C_{1-8}$ alkyl or $C_{5-10}$ aryl group, the $C_{1-8}$ alkyl or $C_{5-10}$ aryl groups being optionally substituted with one or more groups independently selected from halogen atoms, tetrazolyl, $C_{1-8}$ alkyl, $C_{1-8}$ alkoxy, nitro and cyano groups.

According to the invention, $R^2$ can also be a customary leaving group that can couple with a suitably substituted statin group by nucleophilic substitution. Suitable leaving groups are known in organic chemistry. Examples of suitable leaving groups include halogen atoms, especially chlorine, bromine and iodine atoms, and —O—$SO_2$—R wherein R is an alkyl, aryl or alkylaryl group, preferably with no more than 20 carbon atoms. Especially preferably, R is a $C_1$-$C_6$ alkyl group or a $C_5$-$C_{10}$ aryl group, the $C_1$-$C_6$ alkyl group or $C_5$-$C_{10}$ aryl group being optionally substituted with 1 or 2 $C_1$-$C_6$ alkyl groups. Examples of such $C_1$-$C_6$ alkyl group or $C_5$-$C_{10}$ aryl group include a phenyl group, a p-tolyl group or a p-chlorophenyl group. The group —O—$SO_2$—R is especially preferably an O-tos group, wherein tos stands for a tosyl group, or an —O—$SO_2$—$C_6H_4$-p-Cl group.

$R^2$ is especially preferably cyanide, —$CH_2NH_2$ or $SO_2R_6$ group. For all meanings of R and in particular for its preferred meanings, hydroxyl protective group $S^1$ is as defined above.

Compounds of formula I wherein $R^2$ is a halogen atom can be produced preferably directly from compounds of formula I-a. Compounds of formula I wherein $R^2$ is a halogen atom can also be produced from compounds of formula I wherein $R^2$ is another leaving group, in particular O-tosyl or p-chlorophenylsulfonyl. The production of compounds of formula I wherein $R^2$ group is O-tosyl from compounds of formula I-a is known in the state of the art. Compounds of formula I wherein $R^2$ is a halogen atom can be converted into a compound of formula I wherein R is —CH=$P(R_3)_3$, for example, by reaction with a compound $P(R^4)_3$.

Compounds of formula I-a can be converted to, for example, preferred compounds of formula I in accordance with the following scheme:

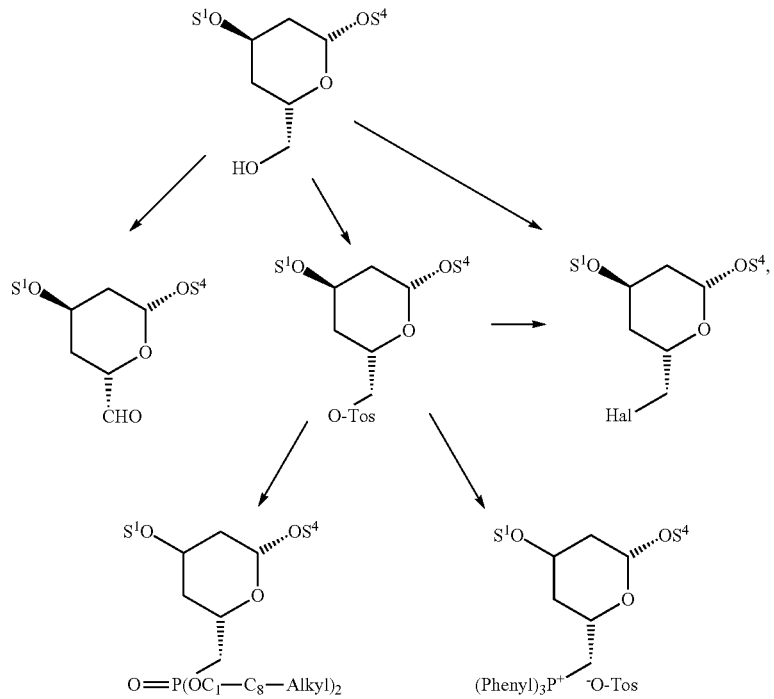

wherein Hal means a halogen atom. If necessary, the group —OS⁴ can be converted by oxidation into a ═O group at any suitable stage of the reaction sequence.

The oxidation of a primary OH group to an aldehyde group can take place, for example, via a Swern oxidation or by oxidation with Cr(VI): $(PyH)_2Cr_2O_7$ (see Handbook of Reagents for Organic Synthesis "Oxidizing and Reducing Agents", ed. S. D. Burke, R. L. Danheiser, John Wiley & Sons Ltd. 1999, S. 330-334) or with Cr(VI): $HPyCrClO_3$ (see Handbook of Reagents for Organic Synthesis "Oxidizing and Reducing Agents", ed. S. D. Burke, R. L. Danheiser, John Wiley & Sons Ltd. 1999, S. 323-330.

The conversion of the tosyl groups into halogenide can take place, for example, as described in Weygand/Hilgetag, 4th edition, 1970, pp. 232-235. The conversion of the tosyl groups into cyanide is described, for example, in Organikum, 16th edition, 1986, 211-216; P. Kurtz in: Houben-Weil, vol. 8, 1952, pp. 290-311; D. T. Mowry, Chem. Rev. 1948, 42, 189-284.

Details about the production of the above compounds can also be gathered, for example, from the following publications:

Journal of the Chemical Society, Perkin Transactions 1: Organic and Bioorganic Chemistry (1972-1999) (1988), (8), 2291-5; (for the aldehydes);
Journal of Organic Chemistry (2001), 66 (20), 6803-6806; (for the tosylate);
Tetrahedron (1995), 51 (48), 13217-38; (for the tosylate);
Journal of the Chemical Society, Perkin Transactions 1: Organic and Bioorganic Chemistry (1995), (13), 1641-3; (for the tosylate);
Journal of Organic Chemistry (1984), 49 (21), 3994-4003; (for the tosylate);
Fujisawa, Kamotsu et al., JP 10087568 A2, 1998, 0407 Heisei; (for the chloride);
Chemistry Letters (1997), (8), 765-766; (for the chloride);
Tetrahedron Letters (1996), 37 (33), 6001-6004; (for the iodide);
Journal of the Chemical Society, Perkin Transactions 1: Organic and Bioorganic Chemistry (1972-1999) (1991), (1), 133-40 (for the iodide); and
Tetrahedron Letters (1988), 29 (38), 4865-8 (for the iodide).

The compound of formula II:

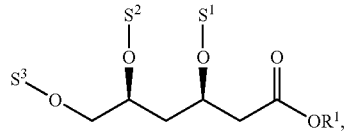

(II)

wherein $S^1$ is a hydroxyl protective group, can be readily produced from compounds of formula II wherein $S^1$ group is a hydrogen atom, for example, by reaction with a compound of formulat $S^1$-A wherein A is a customary leaving group, such as a halogen atom (for example, chlorine, bromine or iodine), and $S^1$ is the hydroxyl protective group.

The especially preferred compound of formula II wherein $S^1$ is t-butyldiphenylsilyl protective group can advantageously be prepared, for example, by reacting with $ClSiPh_2$tert-butyl in a mixture of DMF and imidazole.

Compounds of formula II-a:

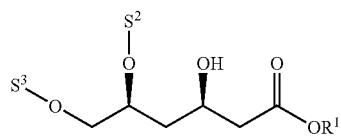

(II-a)

can be produced with high stereoselectivity from compounds of formula III:

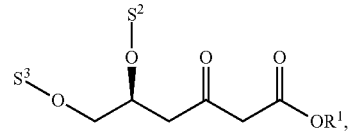

(III)

for example, by hydrogenation with hydrogen at room temperature (25° C.) under elevated pressure in a range of 20 to 80 bar, especially 30 to 70 bar, for example, approximately 50 bar, in a suitable solvent, preferably a polar protic solvent, especially a $C_1$-$C_6$ alcohol such as methanol or ethanol. The hydrogenation preferably takes place with a so-called Ru-BINAP catalyst, as described, for example, in Tetrahedron Lett. 1991, 32, 4163 and in WO 95/18784, which are herein incorporated by reference. Reference is more particularly made to the parts of these publication giving the definition and the production of the preferred catalyst for carrying out the process of the invention.

The catalysts that can be used in accordance with the invention have, for example, the structure:

(R)—Ru(BINAP)Cl₂×NEt₃, and (R)—Ru(BINAP)Cl₂×DMF×NEt₃, wherein ET is ethyl and BINAP has the formula:

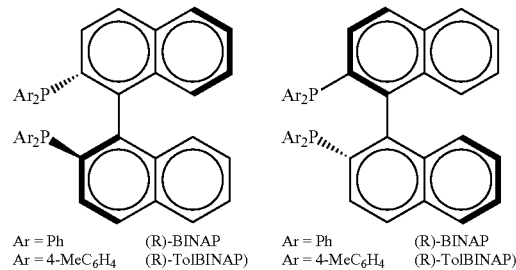

| Ar = Ph | (R)-BINAP | Ar = Ph | (R)-BINAP |
| Ar = 4-MeC₆H₄ | (R)-TolBINAP) | Ar = 4-MeC₆H₄ | (R)-TolBINAP) |

(Ph=Phenyl) and can be produced as described in, for example, Tetrahedron Lett. 1991, 32, 4163. Instead of (R)—BINAP, (R)-Tol BINAP can advantageously be used. With the catalyst (R)—Ru(BINAP)Cl₂×NEt₃, a syn/anti ratio ≧80, especially ≧90, preferably ≧95, more preferably ≧99 can be achieved in the reaction of the invention. This corresponds to a molar ratio of the desired (3R,5S) isomer to the undesired isomer of 80:20 or better. In contrast, a molar ratio of only 78:22 was achieved in the art, such as in, for example, in EP-A 374 922. In addition, it surprisingly turned out that, during the conversion in the presence of catalyst (R)—Ru(TolBINAP) Cl₂×AcONa, the compound of formula II-a obtained is practically stereoisomerically pure. A stereoselective conversion is also obtained with the corresponding (S)-BINAP catalyst. However, in this case, the disadvantageous anti-isomer predominates. Thus, the invention also relates to a process for the stereoselective hydrogenation of a compound of formula III to yield a compound of the formula II-a, in particular using a (R)—RuBINAP or (R)—RuTolBINAP catalyst. These catalysts are as defined above and are described, for example, in WO 95/18784 or in Tetrahedron Lett. 1991, 32, 4163. The hydrogenation supplies a molar ratio between the compound of formula II-a:

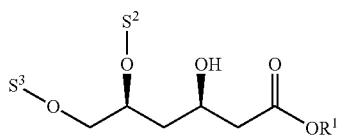

(II-a)

and the corresponding anti-compound:

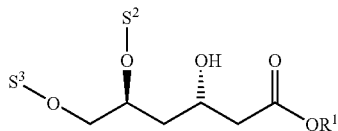

of 80:20 or more, in particular of 90:10 or more, in particular 95:5 or more and most preferably a 99:1 or more. Therefore, it is no longer necessary as a rule in the process of the invention to separate out the undesired anti-isomer. If this should nevertheless be necessary, it can take place in a known manner.

The compound of formula III is readily obtainable, for example, in accordance with the process of Angew. Chem. 1979, 91, 76-77, from the compound of formula IV:

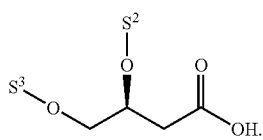

(IV)

Compounds of formula IV can be obtained in a known manner, for example, from the commercially available and economical S malic acid.

The reaction of compound IV to yield compound III advantageously takes place as follow. First, the carboxyl group of compound IV is activated with a suitable activating agent, such as N,N'-carbonyldiimidazole. The activated compound is subsequently reacted with a compound of formula $M^1R^7{}_2X_{0-1}$. In this compound, $M^1$ is a bivalent or trivalent metal cation, especially a metal cation of the second or third main group or of the second or third subgroup of the periodic table of elements, especially a magnesium, calcium, zinc or aluminum ion, especially preferably a magnesium, zinc or aluminum ion ($Mg^{2+}$, $Zn^{2+}$ or $Al^{3+}$ ions). Also, in this compound, $R^7$ is a suitable carboxylic acid group, especially a partially esterified dicarboxylic acid group such as, for example, a $C_{1-4}$—$O_2C(CH_2)_{1-4}CO_2$ group, for example, $EtO_2CCH_2CO_2$. A further example of a suitable $R^7$ group is a $C_{1-6}COO$ group such as $CH_3COO$. The two $R^7$ groups on the metal ion can be identical. However, the two $R^7$ groups can also be different. The X group is an optionally present monovalent counterion that serves for charge compensation if the metal cation $M^1$ is a trivalent ion. It is especially preferable if the two $R^7$ groups are different, for example, if one of the $R^7$ groups is a $C_{1-4}$—$O_2C(CH_2)_{1-4}CO_2$ group and the other group a $C_1$-$C_6COO$ group. Very good results can be achieved, for example, with the compounds $Mg(CH_3COO$—$)(EtO_2CCH_2CO_2$—$)$, $Zn(EtO_2CCH_2CO_2$—$)$ $(EtO_2CCH_2COO$—$)$ or $AlCl(EtO_2CCH_2CO_2$—$)(EtO_2CCH_2COO$—$)$. Other combinations of the above groups are of course also possible. The reaction can take place, for example, at room temperature in THF. Exemplary yields that were achieved are above 60%, and preferably of above 70%.

The metal salts can preferably be produced in situ, for example, by reacting the appropriate metal powder with the appropriate acid (for example $EtO_2CCH_2COOH$) under reflux in a suitable solvent, such as an ether, for example, THF.

All statins comprising the side chain:

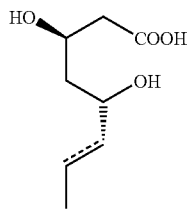

wherein the dotted line represents an optionally present bond, or the corresponding lactones can be produced with the process of the invention.

More specifically, the following preferable statins can be produced:

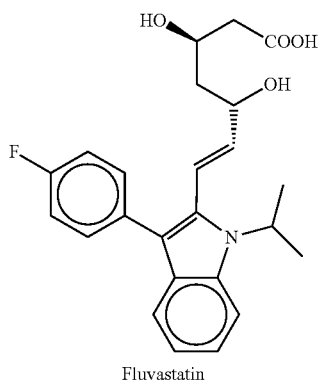

Fluvastatin

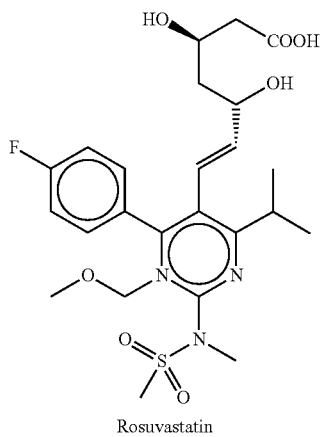

Rosuvastatin

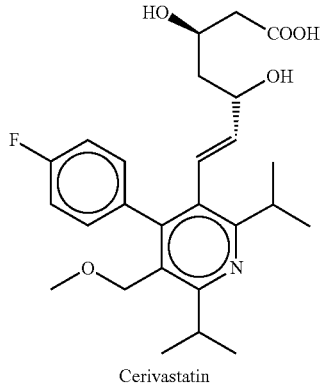

Cerivastatin

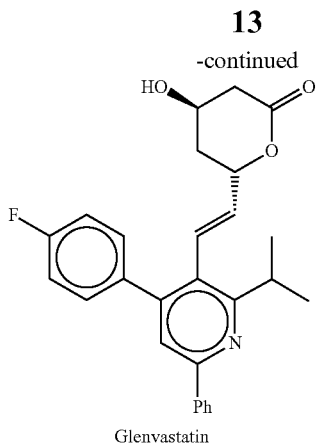

Glenvastatin

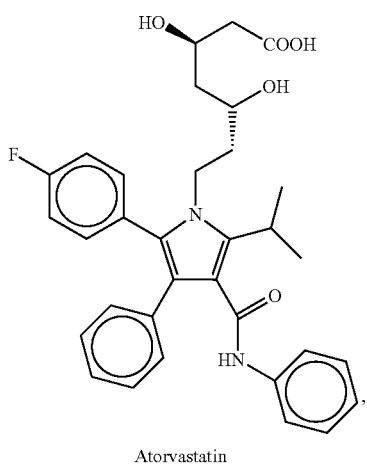

Atorvastatin as well as, for example, itavastatin and BMY22089.

Statins that have the side group:

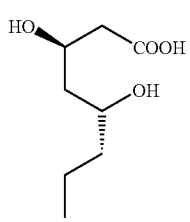

can be obtained by hydrogenation of the corresponding statins containing the side group:

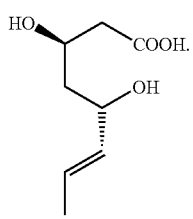

The hydrogenation preferably takes place on a precursor of the statin wherein the hydroxyl group is protected, that is, on the statin with the side chain:

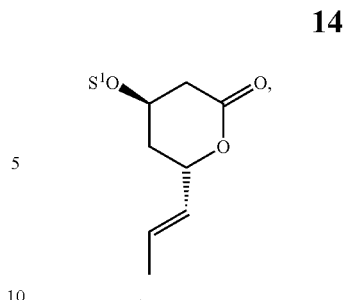

wherein $S^1$ is a hydroxyl protective group as defined above.

The removal of the protective group $S^1$ (if present) and the opening of the lactone ring by hydrolysis preferably take place as the last step of the statin synthesis of the invention.

According to the invention, the coupling of the compound of formula I with the ring system St, which stands for the statin group, preferably takes place by a Wittig reaction or by a Horner-Wittig reaction. The St group is either functionalized with an aldehyde group, in particular when the compound of formula I carries a Wittig- or Horner-Wittig functionality, or is provided with a Wittig- or Horner-Wittig functionality if the compound of formula I carries an aldehyde group. Processes for producing correspondingly functionalized St ring systems are described in, for example, WO 84/02131, EP-A 244 364 and EP 521 471, which are incorporated herein by reference. The functionalized St ring systems that are not expressly cited in these publications can be produced in a corresponding manner. We refer here, for example, to WO 01/04100 and WO 03/006439.

A general process scheme for the production of statins is as follows:

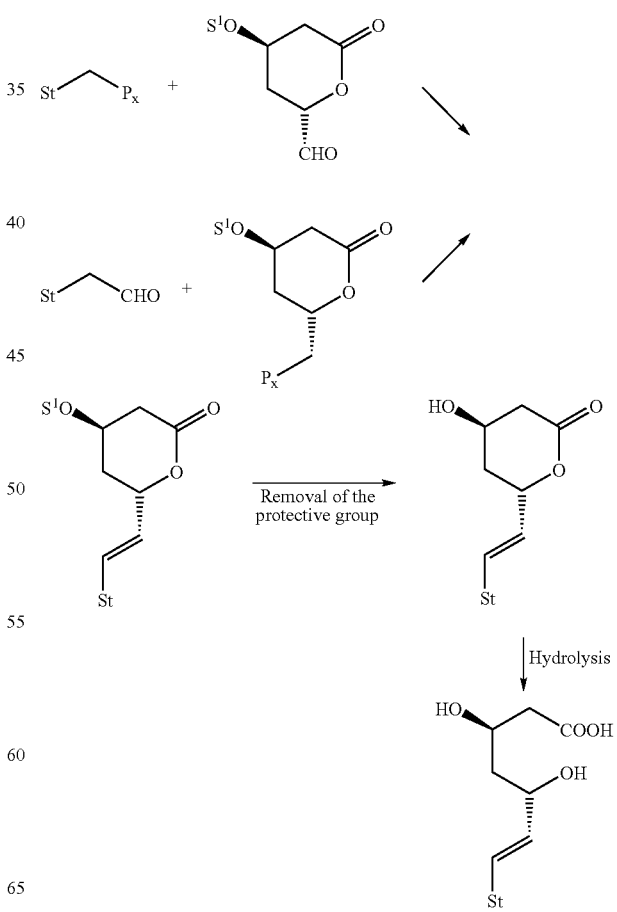

wherein $S^1$ is as defined above and $P_x$ is a Wittig group or a Horner-Wittig group as defined above, in particular a —P$^+$(Phenyl)$_3$$^-$OTos group, and St is the statin group. The statin group may be, for example:

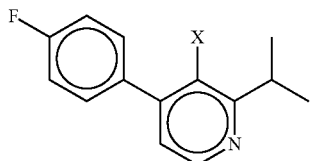

Glenvastatin

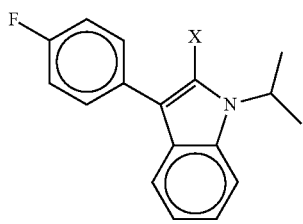

Fluvastatin

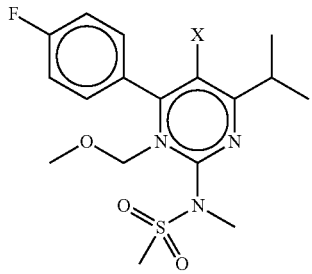

Rosuvastatin

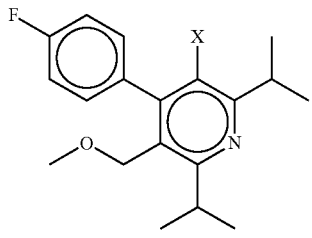

Cerivastatin wherein X shows the bond sites.

In the aforesaid scheme, the $P_x$ group can also be an —S(O)$_2$—R$^6$ group wherein R$^6$ is as defined above.

An exemplary synthesis scheme for the production of atorvastatin is as follows:

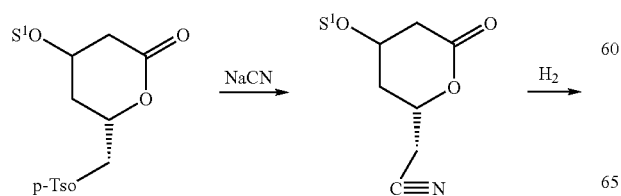

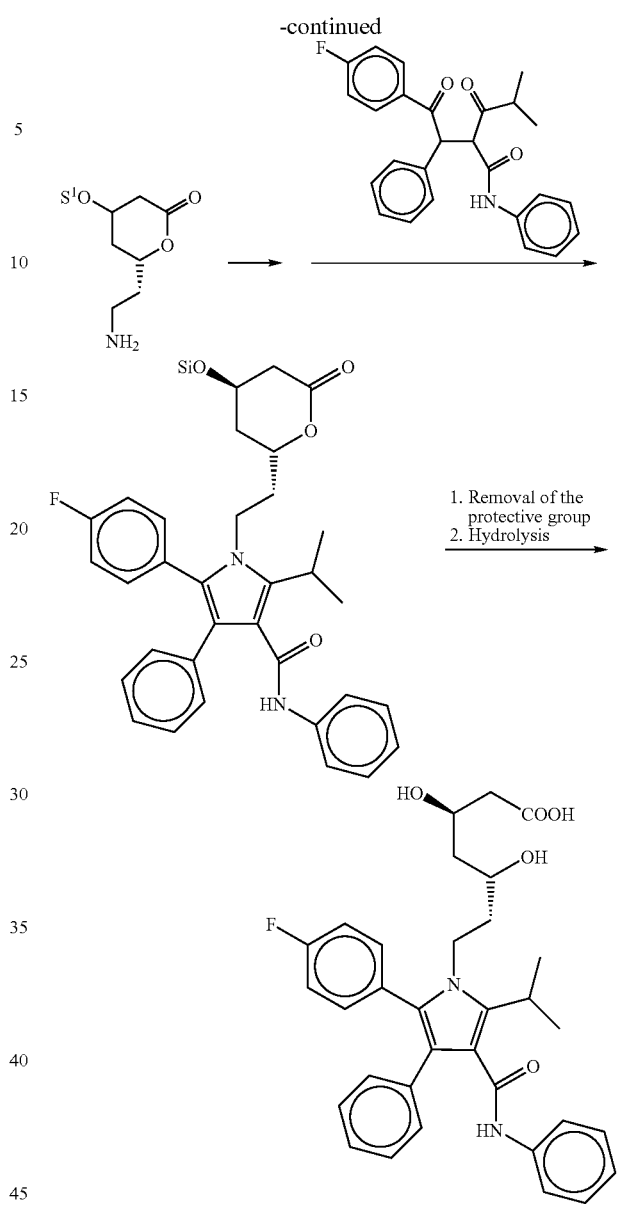

Alternatively, instead of the lactone of formula I, the corresponding lactol, wherein W stands for OS$^4$, can be used. In this case, —OS$^4$ can be oxidized at any suitable position of the reaction sequence to obtain =O.

The diketone

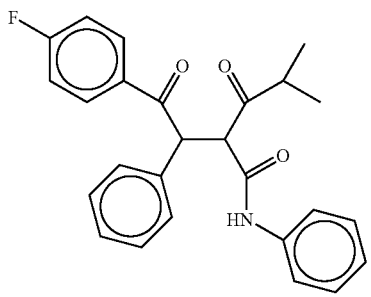

can be produced, for example, as described in WO-A 03/344011, WO-A 03/24959, WO-A 03/04457, WO-A 03/04450, WO-A 01/72706, WO-A 98/04543, U.S. Pat. No. 5,298,627, WO 89/07598 or in Tetrahedron Letters (1992), 33 (17), 2283-4.

Alternatively, instead of the above diketone, a diketone of the following formula can be used:

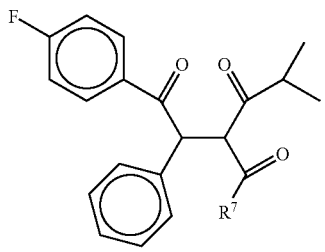

wherein $R^7$ is —$OR^8$, —$NR^9R^{10}$, —$NR^{11}CONR^{12}$—$NR^{13}R^{14}$, —$ONR^{15}R^{16}$ or halogen, and $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ are independently hydrogen or a straight-chain, branched and/or cyclic, saturated or unsaturated $C_{1-10}$ alkyl group or aryl group. Optionally, these alkyl group or aryl group can be substituted with 1-3 optionally protected hydroxy or carboxy groups, 1-3-$OR^{17}$, 1-3-$NR^{18}R^{19}$ and/or 1-3 halogen atoms. The $C_{1-10}$ alkyl group optionally contains 1-3 oxygen atoms, 1-3 nitrogen atoms and/or 1-3-$NR^{20}$. The $C_{1-10}$ alkyl group optionally contains 1 or 2 aryl groups or is substituted by them.

$R^7$ is preferably —$OR^8$ or halogen, especially —$OR^8$. $R^8$ is preferably $C_{1-6}$ alkyl, especially ethyl.

The hydroxylactol of formula I-a can also be used, for example, for the production of rosuvastatin (and similar statins), via a formyllactol intermediate state (see scheme 3):

Scheme 3

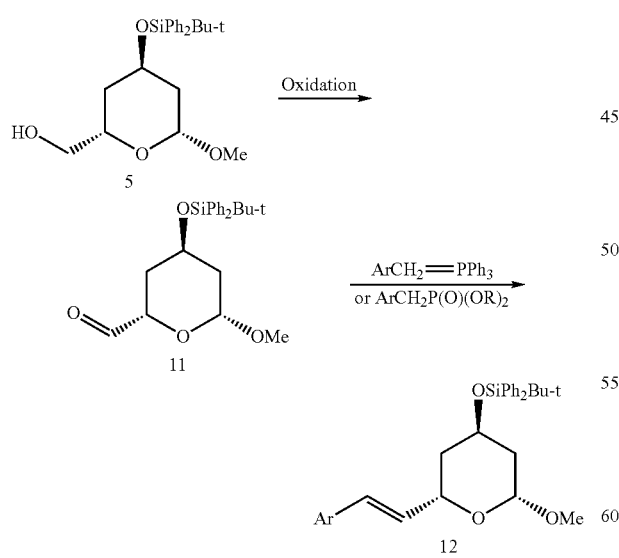

The oxidation of lactol 5 to aldehyde 11 can take place as described in Y.-L. Yang, J. R. Falk, Tetrahedron Lett. 1982, 23, 4305-8. Aldehyde 11 can then be converted into the statin intermediate product 12 as described in, for example, G. Beck, K. Kesseler, E. Baader, W. Bartmann, A. Bergemann in J. Med. Chem. 1990, 33, 52-60.

The following examples illustrate the invention.

EXAMPLES

The following examples refer to the following synthesis scheme indicated by way of example:

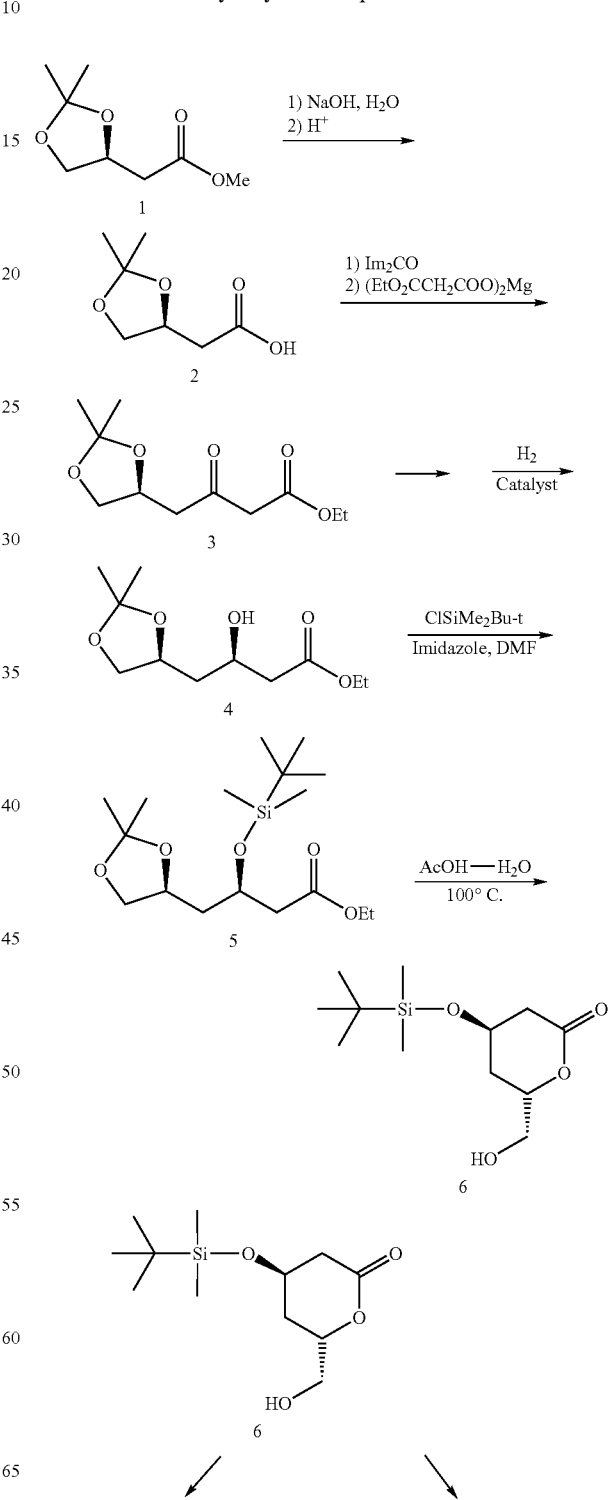

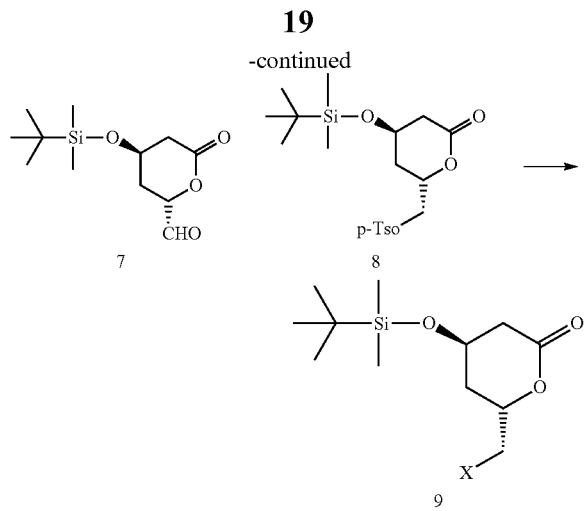

9a X = Cl
9b X = I
9c X = Br
9d X = P⁺Ph₃⁻OTos
9e X = P(O)(OAlk)₂

Example 1

(4S)-(2,2-Dimethyl-1,3-dioxolan-4-yl)acetic acid methylester (Compound 1)

This compound is commercially available, for example, from the Aldrich company, or it can be produced in a simple manner starting from (S)-malic acid dimethylester, in which case one of the ester groups is selectively reduced in accordance with Chem. Letters 1984, 1389-1392 or Tetrahedron 1992, 48, 4067-4086.

0.28 g (0.0074 mol) NaBH₄ were added all at once to a solution of 113.4 g (0.70 mol) of (S) malic acid dimethylester in 300 ml absolute THF. Then, 68 ml (54.5 g, 0.72 mol) of the BH₃×Me₂S complex were slowly added under agitation at room temperature. During the addition, gaseous products developed. After the end of the addition, the reaction mixture was maintained at room temperature for 3 hours. Then, 285 ml methanol were added and the solution obtained was allowed to stand overnight at room temperature. The volatile components were evaporated off and the viscous residue was dried 6 hours under reduced pressure. The residue was mixed with 300 ml acetone, 96.3 ml (81.6 g, 0.78 mol) Me₂C(OMe)₂ and 4 g (0.021 mol) p-TsOH×H₂O. The reaction was agitated overnight at room temperature and was subsequently neutralized with 4 g sodium carbonate. The reaction mixture was agitated for 1 hour, filtered and evaporated. The residue was distilled under reduced pressure (74° C./6 mbar) and 90.6 g (74.4%) of compound 1 were obtained.

Example 2

(4S)-(2,2-dimethyl-1,3-dioxolan-4-yl)acetic acid (Compound 2)

50 g (0.287 mol) of the compound of Example 1 were added under agitation to a 2-molar aqueous sodium hydroxide solution (287 ml, 0.574 mol) cooled with ice. The ice bath was removed and the mixture agitated 2 hours. The mixture was extracted with dichloromethane (3×50 ml) and the organic extracts were separated. The aqueous layer was mixed with 100 ml diethylether and cooled with ice. 300 ml of 2-normal aqueous sodium hydrogen sulfate solution were added to the mixture. The mixture was vigorously agitated 15 minutes. The organic phase was separated off and the aqueous phase extracted with ethyl acetate (2×100 ml). The combined organic phases were dried over sodium sulfate and evaporated. The residue was dried under reduced pressure and 36 g (78.3%) of a liquid product were obtained. The purity of the end product was 95%, as determined by NMR. The product was used without further purification.

¹H NMR (CDCl₃), δ in ppm: 1.37 (3H, s), 1.43 (3H, s), 2.58 (1H, dd, J=16.2 and 6.7 Hz), 2.75 (1H, dd, J=16.2 and 6.7 Hz), 3.68 (1H, dd, J=8.5 and 6.1 Hz), 4.17 (dd, J=8.5 and 6.0 Hz), 4.45-4.53 (1H, m), 11 (1H, br. s).

¹³C NMR (CDCl₃), δ in ppm: 25.8 (CH₃), 27.2, (CH₃), 39.2 (CH₂), 69.4 (CH₂), 72.1 (CH), 109.9 (C), 176.7 (COO).

Example 3

(4S)-(2,2-Dimethyl-1,3-dioxolan-4-yl)-3-oxohexanoic acid ethylester (Compound 3)

A mixture of 49.0 g (0.371 mol) malonic acid monoethylester and 6.0 g (0.248 g-atom) magnesium were heated in 200 ml absolute THF four hours under agitation to reflux, which yielded a first solution. Parallel to the above, 28.8 g (0.177 mol) solid N,N'-carbonylbisimidazole were added during 5 to 10 minutes to a solution of 25.8 g (0.161 mol) of the compound of Example 2 in 100 ml absolute THF, during which a development of gas occurred. The mixture was subsequently agitated at room temperature 2 hours. The remaining magnesium was washed with 50 ml absolute THF and the wash solution was added to the reaction mixture. The reaction mixture was agitated overnight at room temperature. The reaction mixture was evaporated, the residue dissolved in 200 ml ethyl acetate and acidified under vigorous agitation with 430 ml of a 2-normal aqueous solution of sodium hydrogen sulfate. The organic phase was separated off, washed successively with 2-normal aqueous solution of sodium hydrogen sulfate (2×200 ml) and saturated aqueous solution of sodium hydrogen carbonate (3×200 ml), dried over sodium sulfate and evaporated. The residue was distilled under reduced pressure (90 to 90° C., 0.7 mbar) and 26.9 g (72.4%) of compound 3 were obtained. According to the NMR spectra in CDCl₃, the product contained approximately 10% of the enol form. The following NMR spectrum refers exclusively to the keto form.

¹H NMR (CDCl₃), δ in ppm: 1.28 (3H, t, J=7.1 Hz), 1.35 (1H, s), 1.40 (1H, s), 2.75 (1H, dd, J=17.1 and 6.8 Hz), 2.99 (1H, dd, J=17.1 and 6.1 Hz), 3.49 (2H, s), 3.57 (1H, dd, J=8.4 and 6.6 Hz), 4.15-4.24 (3H, m), 4.42-4.52 (1H, m).

¹³C NMR (CDCl₃), δ in ppm: 14.3 (CH₃), 25.7 (CH₃), 27.1 (CH₃), 47.4 (CH₂), 49.9 (CH₂), 61.7 (CH₂), 69.5 (CH₂), 71.7 (CH), 109.2 (C), 167.1 (COO), 201 (C=O).

Example 4

(3R,4S)-(2,2-Dimethyl-1,3-dioxolan-4-yl)-3-hydroxyhexanoic acid ethylester (Compound 4)

a) Production of the Catalyst

A mixture of 200 mg (0.295 mmol) (R)-TolBINAP, 73.6 mg (0.147 mmol) [Ru(C₆H₆)Cl₂]₂ and 2 ml DMF was agitated 15 minutes under argon at 100° C. The volatile components were evaporated off and the residue dried 1 hour under reduced pressure at 50° C. This process for the production of BINAP catalysts is based on that published in Tetrahedron Lett. 1991, 32, 4163. The residue was dissolved in 3 ml dichloromethane and 0.2 ml triethyl amine was added. After 1 hour at room temperature, the volatile components were evaporated and the residue dried under reduced pressure. The solid product was used, without further purification and characterization, as a catalyst in the following hydrogenation.

b) Hydrogenation of the Ketone of Example 3

A mixture of 0.58 g (2.5 mol) of the complex of Example 3, 4.3 mg (ca. 0.0005 mmol) of the precatalyst produced in step a) and in 10 ml absolute oxygen-free methanol was hydrogenated under an initial 50 bar hydrogen pressure at room temperature under agitation and under anaerobic conditions. After 150 minutes, the absorption of hydrogen ended. The autoclave was opened and the mixture evaporated and dried under reduced pressure. The reaction and the yield were quantitative. According to the NMR spectra, the diastereomeric purity of the product was greater than 99%. The diastereomeric purity was determined using the NMR spectra by analogy with the corresponding methyl esters according to Chem. Ber. 1998, 2035-2044.

$^1$H NMR (CDCl$_3$), δ in ppm: 1.27 (3H, t, J=7.1 Hz), 1.36 (3H, s), 1.42 (3H, s), 1.72-1.83 (2H, m), 2.45-2.59 (2H, m), 3.53-3.61 (2H, m), 4.08-4.35 (5H, m).

$^{13}$C NMR (CDCl$_3$), δ in ppm: 14.4 (CH$_3$), 25.9 (CH$_3$), 27.1 (CH$_3$), 39.9 (CH$_2$), 41.8 (CH$_2$), 60.8 (CH$_2$), 67.0 (CH), 69.7 (CH$_2$), 74.6 (CH), 109.4 (C), 172.3 (COO).

Example 5

(3R,4S)-(2,2-Dimethyl-1,3-dioxolan-4-yl)-3-(tert-butyldimethylsilyloxy)hexanoate (Compound 5)

The title compound was obtained with a yield of 88% from the compound of Example 4 according to the instructions in J. Org. Chem. 1984, 49, 3994-4003.

Example 6

(4R,6S)-4-(tert-Butyldimethylsilyloxy)-6-hydroxymethyltetrahydropyran-2-one (Compound 6)

The title compound was obtained with a yield of 60% from the compound of Example 5 according to the process in J. Org. Chem. 1984, 49, 3994-4003.

Example 7

(4R,6S)-4-(tert-Butyldimethylsilyloxy)-6-(p-toluolsulfonyloxymethyl)tetrahydropyran-2-one (Compound 8)

The title compound was obtained with a yield of 91% from the compound of Example 6 according to the process in J. Org. Chem. 1984, 49, 3994-4003.

The following examples refer to the following reaction schemes 1 and 2:

Scheme 1

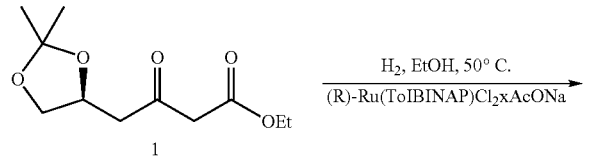

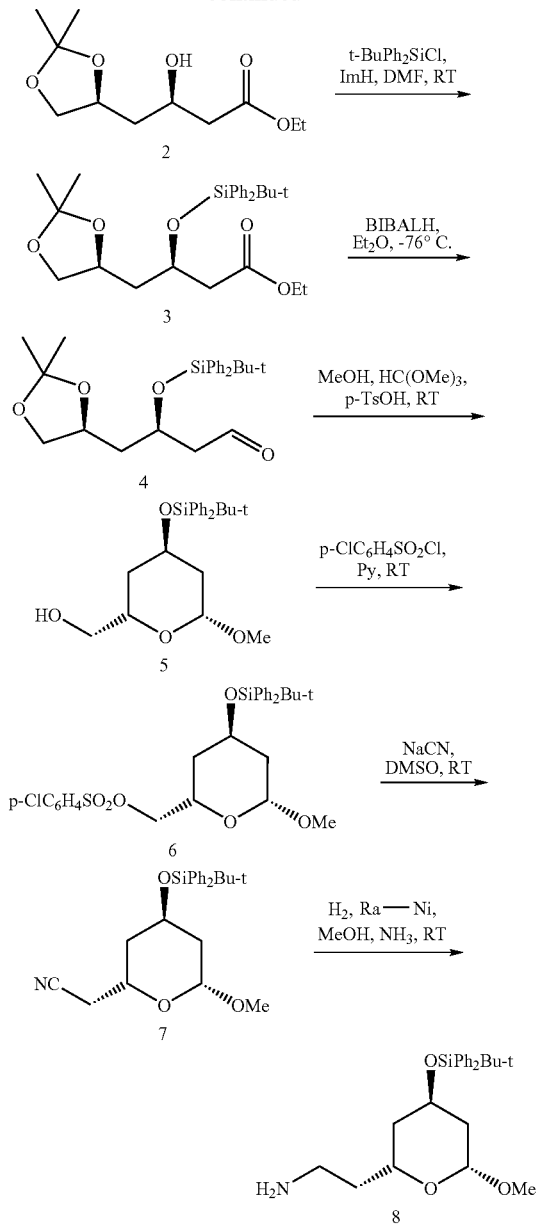

Scheme 2

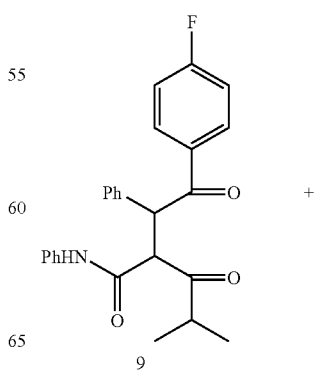

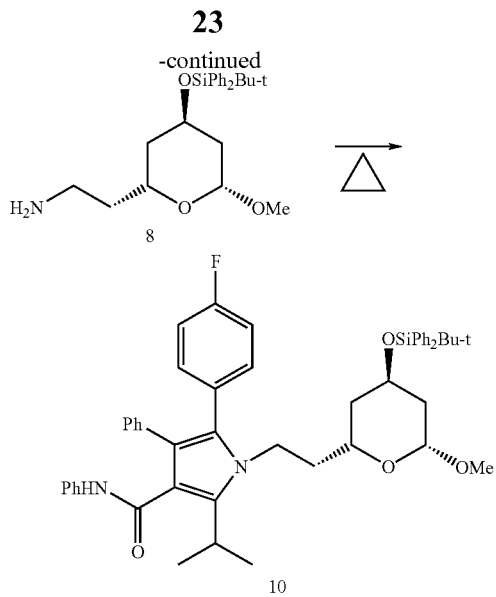

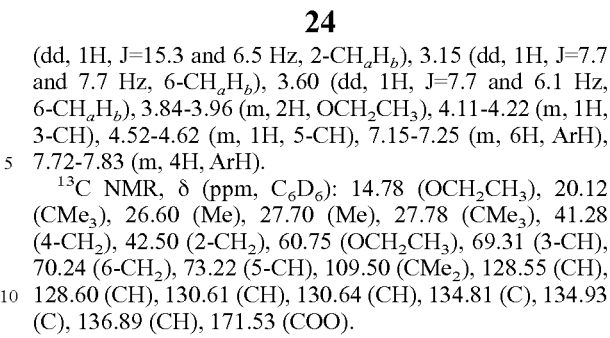

Example 8

Ethyl (3R,5S)-3-hydroxy-5,6-(isopropylidenedioxy)hexanoate (2)

a) Catalyst Production

A mixture of 200 mg (0.295 mmol) of (R)-TolBINAP, 73.6 mg (0.147 mmol) [Ru(C$_6$H$_6$)Cl$_2$]$_2$, 24.2 mg AcONa and 2 ml DMF were agitated at 100° C. for 15 minutes under argon. The volatile components were evaporated and the residue dried in a vacuum at 50° C. for one hour. The solid material was used as catalyst for the following hydrogenation without further purification and characterization.

b) Hydrogenation of the β-keto Ester 1

A mixture of 3.5 g (15.2 mmol) of β-keto ester 1 and 9.4 mg (ca. 0.01 mmol) of the above catalyst were placed in a 50 ml autoclave and freed of oxygen by three vacuum argon cycles. Then, 8 ml absolute, oxygen-free EtOH were added and the mixture agitated under 100 bar initial H$_2$ pressure at 50° C. The consumption of H$_2$ stopped after approximately 4 hours. The autoclave was opened and the mixture concentrated by evaporation in a vacuum and dried. The conversion and yield were quantitative. The obtained compound 2 was used without further purification.

Example 9

Ethyl (3R,5S)-3-tert-butyldiphenylsilyloxy-5,6-(isopropylidenedioxy)hexanoate (3)

A solution of 4.0 g (0.0172 mol) of alcohol 2 and 2.5 g (0.0367 mol) imidazole in 8 ml DMF was cooled with water (10-15° C.) and 2.5 ml (5.5 g, 0.020 mol) t-BuPh$_2$SiCl were added under agitation. The reaction mixture was agitated overnight at room temperature. It was diluted with water and AcOEt under agitation. The organic layer was separated off. The aqueous phase was additionally extracted with AcOEt. The combined organic extracts were washed with saline solution, dried over Na$_2$SO$_4$ and concentrated by evaporation. The residue was chromatographed on SiO$_2$ (35×8 cm column, elution agent: hexane-AcOEt 9:1). The yield of the title product (very viscous colorless oil) was 7.63 g (94.1%).

$^1$H NMR, δ (ppm, C$_6$D$_6$): 0.92 (t, 3H, J=7.1 Hz, OCH$_2$CH$_3$), 1.15 (s, 9H, CMe$_3$), 1.23 (s, 3H, Me), 1.24 (s, 3H, Me), 1.63-1.74 (m, 1H, 4-CH$_a$H$_b$), 1.77-1.87 (m, 1H, 4-CH$_a$H$_b$), 2.60 (dd, 1H, J=15.3 and 5.9 Hz, 2-CH$_a$H$_b$), 2.66 (dd, 1H, J=15.3 and 6.5 Hz, 2-CH$_a$H$_b$), 3.15 (dd, 1H, J=7.7 and 7.7 Hz, 6-CH$_a$H$_b$), 3.60 (dd, 1H, J=7.7 and 6.1 Hz, 6-CH$_a$H$_b$), 3.84-3.96 (m, 2H, OCH$_2$CH$_3$), 4.11-4.22 (m, 1H, 3-CH), 4.52-4.62 (m, 1H, 5-CH), 7.15-7.25 (m, 6H, ArH), 7.72-7.83 (m, 4H, ArH).

$^{13}$C NMR, δ (ppm, C$_6$D$_6$): 14.78 (OCH$_2$CH$_3$), 20.12 (CMe$_3$), 26.60 (Me), 27.70 (Me), 27.78 (CMe$_3$), 41.28 (4-CH$_2$), 42.50 (2-CH$_2$), 60.75 (OCH$_2$CH$_3$), 69.31 (3-CH), 70.24 (6-CH$_2$), 73.22 (5-CH), 109.50 (CMe$_2$), 128.55 (CH), 128.60 (CH), 130.61 (CH), 130.64 (CH), 134.81 (C), 134.93 (C), 136.89 (CH), 171.53 (COO).

Example 10

(3R,5S)-3-tert-Butyldiphenylsilyloxy-5,6-(isopropylidenedioxy)hexanal (4)

A solution of 4.31 g (0.00916 mol) of ester 3 in 18 ml Et$_2$O was cooled to −78° C. and 6.7 ml (0.0101 mol) of a 1.5M solution of DIBALH in toluene was added in 5 minutes. The reaction mixture was maintained for a further 10 minutes under the same conditions. Then, 10 ml MeOH were added. The cooling bath was removed and the mixture agitated for two hours at room temperature. The precipitate formed was filtered off and washed with Et$_2$O. The combined wash solutions were concentrated by evaporation and the product (a thick oil) used in the next step without additional purification. The purity was confirmed by TLC (SiO$_2$, hexane-AcOEt 9:1).

$^{13}$C NMR, δ(ppm, C$_6$D$_6$): 20.04 (CMe$_3$), 26.57 (Me), 27.66 (Me), 27.75 (CMe$_3$), 41.45 (4-CH$_2$), 50.81 (2-CH$_2$), 67.94 (3-CH), 70.22 (6-CH$_2$), 72.98 (5-CH), 109.61 (CMe$_2$), aromatic C were omitted, 200.60 (CHO).

Example 11

(2S,4R,6S)-2-Hydroxymethyl-4-tert-butyldiphenylsilyloxy-6-methoxytetrahydropyrane (5)

Aldehyde 4 was dissolved in 8 ml MeOH and 4 ml HC(OMe)$_3$ were added, followed by 0.2 g TsOH×Py. The solution obtained was placed in a hot bath (70-80° C.) and maintained under reflux for 1 hour. After cooling off, water and a saturated solution of NaHCO were added and the product extracted with AcOEt. The combined extracts were dried over Na$_2$SO$_4$ and concentrated by evaporation. The residue was triturated with hexane in order to effect crystallization. The mixture was stored overnight in a refrigerator. The solid product 5 was filtered off and dried. The yield was 2.09 g (53.5%) (calculated on the starting ester 3). (Almost the same yield of raw material 5 was obtained using TsOH as catalyst in the same mixture at room temperature overnight).

The analysis specimen was produced by recrystallization from hexane.

m.p. 94-5° C. ([Lit. (Y.-L. Yang, J. R. Falk, Tetrahedron Lett. 1982, 23, 4305-4308); m.p. 97° C.-98° C.].

$[α]_D^{22}$ −21.2 (c 4.03, CHCl$_3$) [Lit: (Y.-L. Yang, J. R. Falk, Tetrahedron Lett. 1982, 23, 4305-4308)

$[α]_D^{24}$ −11.2 (c 4.03, CHCl$_3$); (A. P. Kozikowski, C.-S. Li, J. Org. Chem., 1985, 50, 778-785)

$[α]_D^{24}$ −11.3 (c 0.195, CHCl$_3$)].

$^1$H NMR, δ (ppm, C6D6): 1.13 (s, 9H, CMe3), 1.15-1.25 (m, 1H, H of CH2), 1.29-1.38 (m, 1H, H of CH2), 1.39-1.48 (m, 1H, H of CH2), 1.87-1.97 (m, 1H, H of CH2), 2.18 (broad s, 1H, OH), 3.35 (s, 3H, OMe), 3.39 (m, 1H, OCHaHb), 3.52-3.62 (m, 1H, OCHaHb), 4.11-4.22 (m, 2H, 2-CH+4-CH), 5.02 (dd, 1H, J=9.5 and 2.2 Hz, 6-CH), 7.13-7.25 (m, 6H, ArH), 7.62-7.70 (m, 4H, ArH).

$^{13}$C NMR, δ (ppm, C6D6): 20.01 (CMe3), 27.81 (CMe3), 35.02 (CH2), 39.75 (CH2), 56.52 (OMe), 66.44 (OCH2), 68.00 (CH), 72.26 (CH), 100.6 (OCHO), aromatic C omitted.

Example 12

(2R,4R,6S)-2-Cyanomethyl-4-tert-butyldiphenylsilyloxy-6-methoxytetrahydropyrane (7)

A solution of 2.26 g (0.0564 mol) of lactol 5 in 6 ml pyridine was cooled with ice water and 1.5 g (0.00711 mol) p-ClC6H4SO2Cl were added under agitation. After one hour, the bath was removed and the mixture agitated overnight at room temperature. Water (1 ml) was added and the mixture agitated 1 hour further in order to destroy excess sulfochloride. The mixture was diluted with water and the product extracted with AcOEt. The organic extract was washed successively with saline solution, ca. 2N HCl (until the wash solutions remained acidic) and solution of common salt, dried over Na2SO4 and concentrated by evaporation in order to yield (2S,4R,6S)-2-(p-chlorobenzolsulfonyloxy)methyl-4-tert-butyldiphenylsilyloxy-6-methoxytetrahydropyrane (6) as a slightly yellow, thick oil that was dissolved in 9 ml DMSO. After the addition of 1.1 g (0.0224 mol) NaCN, the mixture was agitated 4 hours at room temperature. The mixture was diluted with water and agitated for a further hour in order to dissolve organic materials. Non-soluble materials were filtered off, washed with water and dried in a vacuum. The brownish solid product was dissolved in benzene-AcOEt (10:1) in filtered through a plug of SiO2 in order to remove colored impurities. The SiO2 was washed with the same mixture and the wash solutions concentrated by evaporation. The residue was recrystallized from hexane-EtOH. After standing overnight in a refrigerator, the crystals were filtered off, washed with hexane and dried in air in order to yield 1.71 g (74.0% calculated on the starting lactol 5) colorless crystalline cyano-lactol 7.

M.p. 129-30° C.

$[\alpha]_D$22-23.0 (c 1, EtOH).

1H NMR, δ (ppm, C6D6): 0.80-0.90 (m, 1H, H of CH2), 1.11 (s, 9H, CMe3), 1.24-1.38 (m, 2H, H+H of CH2), 1.70 (dd, 1H, J=16.6 and 5.9 Hz, CHaHbCN), 1.77 (dd, 1H, J=16.6 and 6.5 Hz, CH3HbCN), 1.81-1.89 (m, 1H, H of CH2), 3.34 (s, 3H, OMe), 3.94-4.04 (m, 2H, 2-CH+4-CH), 4.88 (dd, 1H, J=9.4 and 2.1 Hz, 6-CH), 7.12-7.27 (m, 6H, ArH), 7.58-7.67 (m, 4H, ArH).

13C NMR, δ (ppm, C6D6): 19.96 (CMe3), 24.46 (CH2CN), 27.77 (CMe3), 38.02 (CH2), 39.12 (CH2), 56.56 (OMe), 67.15 (CH), 67.46 (CH), 100.59 (OCHO), 117.56 (CN), aromatic C omitted.

Anal. calculated for C24H31NO3Si: C, 70.38; H, 7.63; N, 3.42. Observed: C, 70.79; H, 7.42; N, 3.36.

Example 13

(2R,4R,6S)-2-Aminomethyl-4-tert-butyldiphenylsilyloxy-6-methoxytetrahydropyrane (8)

A 30 ml autoclave was charged with 0.52 g (0.00127 mol) cyano-lactol 7, Ni—Ra (0.25 g wet catalyst was washed three times with ethanol before the hydrogenation), 8 ml MeOH and 2 ml 7N ammonia methane solution. The hydrogenation was carried out at 50 bar initial H2 pressure and room temperature. After 5 hours, the consumption of H2 stopped. The catalyst was decanted and washed with MeOH. The methanol was concentrated by evaporation. The residue was dissolved in MeOH and the solution filtered through a small Celite plug in order to remove small particles of the catalyst. The Celite was washed with MeOH. The clear solution was concentrated by evaporation and dried in a vacuum in order to obtain amine lactol as colorless thick oil. The yield was quantitative.

Anal. Calculated for C23H32O4Si: C, 68.96; H, 8.05. Observed: C, 69.43; H, 8.10.

1H NMR, δ (ppm, CDCl3): 1.089 (s, 9H, CMe3), 1.2-1.9 (complex multiplets, 8H, 4 CH2), 3.51 (s, 3H, OMe), 4.01-4.15 (m, 1H, CH9), 4.22-4.32 (m, 1H, CH), 4.83 (dd, 1H, J=9.6 and 1.9 Hz, OCHO), 7.33-7.47 (m, 6H, ArH), 7.59-7.68 (m, 4H, ArH).

$^{13}$C NMR, δ (ppm, CDCl$_3$): 19.52 (CMe$_3$), 37.31 (CMe$_3$), 38.89 (CH$_2$), 38.96 (CH$_2$) 56.44 (OMe), 67.35 (CH), 69.53 (CH), 99.94 (OCHO), aromatic C omitted.

Example 14

Pyrrole 10

A mixture of 0.48 g (0.0016 mol) of amine lactol 8, 0.5 g (0.00120 mol) diketone 9, 0.1 g (0.000979 mol), pivalic acid and 5 ml solvent (heptane-THF-MePh 100:50:60) was boiled 30 hours under reflux under a slow current of argon. After having cooled off, the mixture was diluted with AcOEt and successively washed with a saturated NaHCO$_3$ solution and saline solution, dried over Na$_2$SO$_4$ and concentrated by evaporation. A chromatograph of the solid residue of SiO$_2$ (eluent: hexane-AcOEt 5:1) yielded 0.66 g (71.6%) pyrrol 10 as yellowish solvent.

$^1$H NMR, δ (ppm, C$_6$D$_6$) only for characteristic signals: 1.11 (s, 9H, CMe$_3$), 1.74 (d, 3H, J=7.1 Hz, CHMe$_a$), 1.75 (d, 3H, J=7.1 Hz, CHMe$_b$), 3.33 (s, 3H, OMe), 3.71 (7 lines, 1H, J=7.1, CHMe$_2$), 3.83-3.98 (m, 2H, CH$_2$N), 4.91 (dd, 1H, J=9.6 and 1.9 Hz, OCHO).

$^{13}$C NMR, δ (ppm, C$_6$D$_6$): 19.94 (CMe$_3$), 22.53 (CHMe$_a$), 22.69 (CHMe$_b$), 27.36 (CHMe$_2$), 27.77 (CMe$_3$), 38.56 (CH$_2$), 38.60 (CH$_2$), 39.54 (CH$_2$), 42.15 (CH$_2$), 56.17 (OMe), 68.00 (CH), 68.47 (CH), 100.33 (OCHO), aromatic C omitted.

What is claimed is:

1. A process for the production of a statin comprising one of the following steps:

a) reducing a compound of formula II:

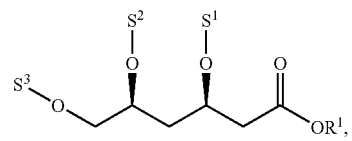

(II)

wherein, $S^1$ is hydrogen or a hydroxyl protective group, $S^2$ and $S^3$ are independently hydroxyl protective groups, and $R^1$ is hydrogen or a carboxyl protective group, to yield a compound of formula VI:

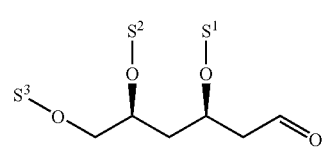

(VI)

or b) lactonizing a compound of formula II:

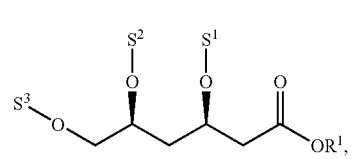

(II)

wherein S¹, S², S³, and R¹ are as defined above, and subsequently reducing the lactone to yield a compound of formula I-a:

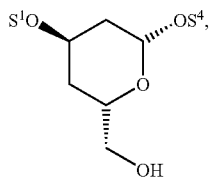
(I-a)

wherein S⁴ is a hydrogen or a hydroxyl protective group.

2. The process according to claim 1, further comprising:
c) lactolizing the compound of formula VI to yield a compound of formula I-a:

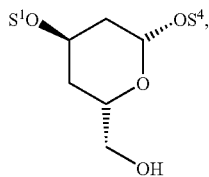
(I-a)

wherein S⁴ is hydrogen or a hydroxyl protective group.

3. The process according to claim 2, further comprising:
d) converting the compound of formula I-a:

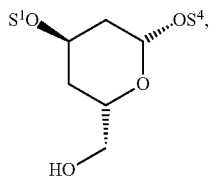
(I-a)

into a compound of formula I:

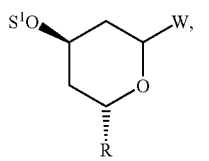
(I)

wherein
S¹ is defined in claim 1 hydrogen or a hydroxyl protective group,
W is =O or —OS⁴, wherein S⁴ is hydrogen or a hydroxyl protective group,
R is —CH₂R², —CHO, —CH=P(R³)₃, —CH₂—P⁺(R³)₃M⁻,

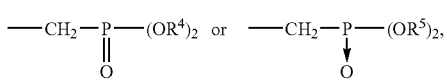

R² is a halogen atom, —C≡N, —CH₂NH₂, —SO₂—R⁶ or a leaving group,
R³, R⁴, and R⁵ complete a Wittig group or a Horner-Wittig group,
R⁶ is hydrogen or a C₁₋₃-alkyl- or C₅₋₁₀ aryl group that is optionally substituted with one or more groups independently selected from halogen atoms, heterocycles that contain 1 to 5 carbon atoms and 1 to 5 heteroatoms selected from sulfur, nitrogen and oxygen atoms, and functional groups, and
M⁻ is a counterion.

4. The process according to claim 1, wherein the compound of formula

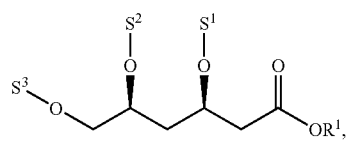
(II)

wherein S¹, S², S³ and R¹ are as defined in claim 1, is produced by stereoselective hydrogenation of a compound of formula III:

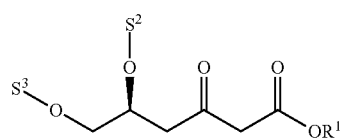
(III)

to yield a compound of formula

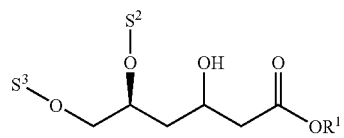
(II-a)

wherein a hydroxyl protective group may be optionally introduced.

5. The process according to claim 4, wherein the hydrogenation is carried out in the presence of catalyst (R)—Ru(TolBINAP)Cl₂×AcONa.

6. The process according to claim 4, wherein the compound of formula III:

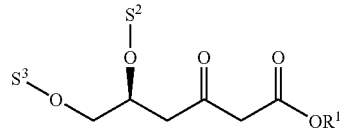
(III)

wherein
S² and S³ are independently hydroxyl protective groups, and
R¹ is hydrogen or a carboxyl protective group,
is produced by chain lengthening of a compound of formula IV:

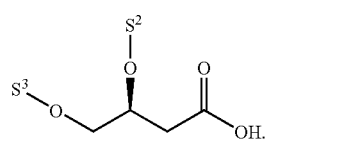
(IV)

7. The process according to claim 3, wherein the compound of formula I is converted into the statin by one of the following process steps and subsequently optionally opening the lactone ring and optionally removing protective groups:

a) reacting a compound of formula I:

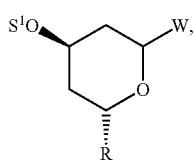
(I)

wherein R is CHO, $S^1$ is hydrogen or a hydroxyl protective group and W is =O or —$OS^4$, wherein $S^4$ is hydrogen or a hydroxyl protective group, with a compound of formula:

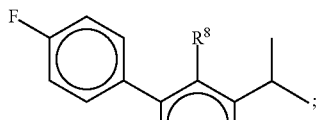

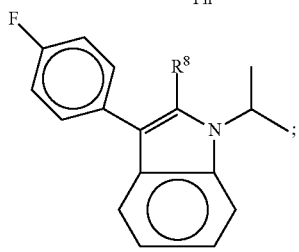

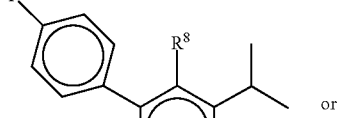
or

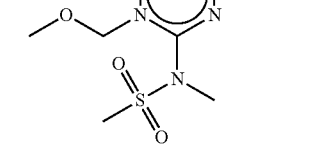

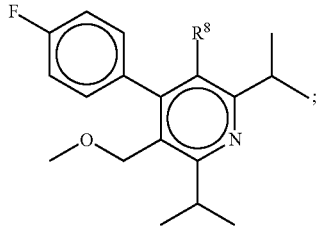

wherein
$R^8$ is —CH=P($R^3$)$_3$, —$CH_2$—$P^+$($R^3$)$_3M^-$,

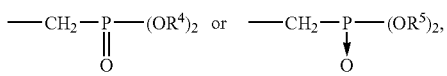

wherein $R^3$, $R^4$, $R^5$, and M are as defined in claim 3;
b) reacting a compound of formula I:

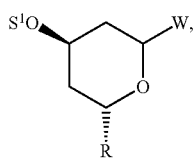
(I)

wherein R is —CH=P($R^3$)$_3$, —$CH_2$—$P^+$($R^3$)$_3M^-$,

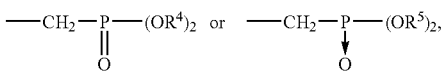

$S^1$ is hydrogen or a hydroxyl protective group and W is =O or —$OS^4$, wherein $S^4$ is hydrogen or a hydroxyl protective group,
with a compound of formula:

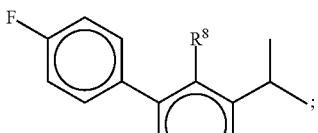

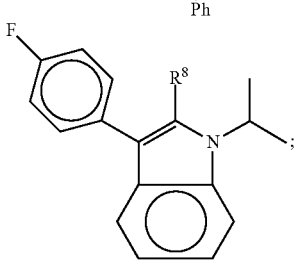

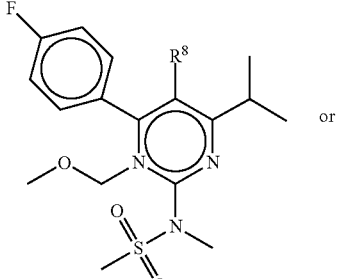
or

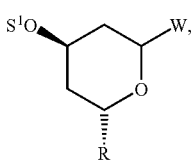

wherein
$R^8$ is —CHO, and
$R^3$, $R^4$, $R^5$, and M are as defined in claim 3;
c) hydrogenating a compound of formula I:

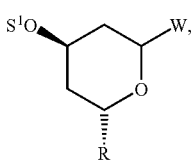
(I)

wherein R is —$CH_2$—C≡N, $S^1$ is hydrogen or a hydroxyl protective group and W is =O or —$OS^4$, wherein $S^4$ is hydrogen or a hydroxyl protective group, to yield a compound of formula I, wherein R is —$CH_2$—$CH_2NH_2$, with a compound of formula V:

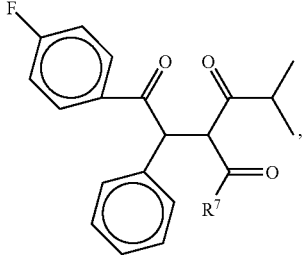

wherein $R^7$ is —$OR^8$, —$NR^9R^{10}$, or halogen, and $R^8$, $R^9$, and $R^{10}$ are independently hydrogen or a straight-chain, branched and/or cyclic, saturated or unsaturated $C_{1-10}$ alkyl group or aryl group, wherein the $C_{1-10}$ alkyl group or aryl group is optionally substituted with 1-3 optionally protected hydroxy- or carboxy groups, 1-3 alkoxy groups, 1-3 alkylamino groups and/or 1-3 halogen atoms, wherein the $C_{1-10}$ alkyl group optionally contains 1-3 oxygen atoms, and/or 1-3 nitrogen atoms and wherein the $C_{1-10}$ alkyl group optionally contains 1 or 2 aryl groups or is substituted by them; and d) reacting a compound of formula (I):

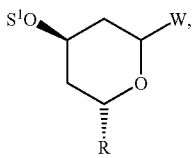

wherein R is —$CH_2$—$CH_2NH_2$, $S^1$ is hydrogen or a hydroxyl protective group and W is =O or —$OS^4$, wherein $S^4$ is hydrogen or a hydroxyl protective group, with a compound of formula V:

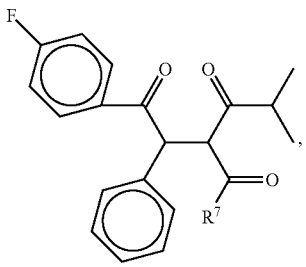

wherein $R^7$ is as defined above, wherein W, when it stands for —$OS^4$, can be oxidized to =O at any suitable position of one of the reaction step a) to d), and wherein, in the reaction sequences c) and d), $R^7$, if it is not an amine, can be converted by aminolysis into an amine at any suitable position of the reaction sequence.

8. The process according to claim 1, characterized in that a compound of formula:

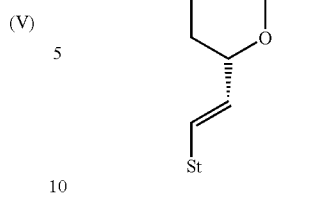

wherein $S^1$ is hydrogen or a hydroxyl protective group and W is =O or —$OS^4$, wherein $S^4$ is hydrogen or a hydroxyl protective group and St stands for the statin group;

is converted by catalytic hydrogenation into a compound of the formula:

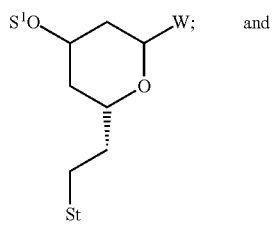
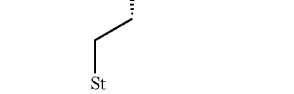

and further wherein $S^1$ is optionally removed, W is optionally converted, when it stands for —$OS^4$, into =O, and the lactone ring is optionally opened.

9. The process according to claim 1, wherein $S^1$ is selected from the group consisting of trimethylsilyl, triisopropylsilyl, trimethylsilylethyl, tert-butyldimethylsilyl, tert-butylmethylsilyl, di-tert-butylmethylsilyl, tert-butyldiphenylsilyl, triphenylsilyl, diphenylmethylsilyl, tris(trimethylsilyl)silyl and para-tosyl protective group.

10. The process according to claim 1, wherein $S^2$ and $S^3$ are bridged.

11. The process according to claim 10, wherein $S^2$ and $S^3$ jointly represent an isopropylidene protective group.

12. The process according to claim 3, wherein R is —$CH_2R^2$ and $R^2$ is a leaving group, wherein said leaving group is a halogen atom, —$OSO_2$—$C_1$-$C_6$ alkyl, or —$OSO_2$—$C_5$-$C_{10}$ aryl.

13. The process according to claim 3, wherein $R^1$ group is a hydrogen atom, $C_{1-3}$ alkyl- or $C_{4-10}$ aryl group, wherein the $C_{1-3}$ alkyl- or $C_{4-10}$ aryl group is optionally substituted by one or more groups independently selected from halogen atoms, heterocycles containing 0 to 10 carbon atoms and 1 to 10 heteroatoms selected from sulfur, nitrogen and oxygen atoms, and functional groups.

14. The process according to claim 3, wherein $R^3$ is a $C_5$-$C_{10}$ aryl group optionally substituted by one or two $C_1$-$C_4$ alkyl groups and/or halogen atoms, a $C_1$-$C_4$ alkyl group or a $C_5$-$C_{10}$ cycloalkyl group, $R^4$ is $C_1$-$C_4$ alkyl, $R^5$ is $C_1$-$C_6$ alkyl or $C_5$-$C_{10}$ aryl.

15. The process according to claim 1, wherein the statin is selected from the group consisting of fluvastatin, rosuvastatin, cerivastatin, glenvastatin, and atorvastatin.

16. A process for producing a compound of formula II:

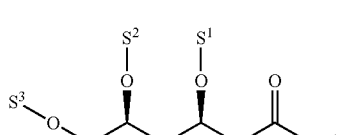

wherein:
$S^1$ is hydrogen or a hydroxyl protective group,
$S^2$ and $S^3$ are independently hydroxyl protective groups, and
$R^1$ is hydrogen or a carboxyl protective group,
comprising the steps of: hydrogenating a compound of formula III:

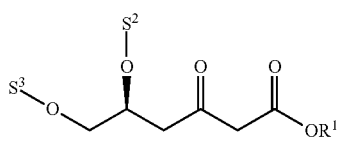

in the presence of catalyst (R)—Ru(TolBINAP)Cl$_2$× AcONa, and
optionally introducing a hydroxyl protective group.

17. A process for producing a compound of formula I-a:

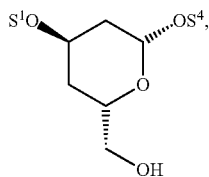

wherein $S^1$ is hydrogen or a hydroxyl protective group and $S^4$ is hydrogen or a hydroxyl protective group, comprising the steps of:
lactolizing a compound of formula VI:

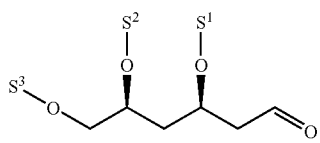

wherein
$S^1$ is hydrogen or a hydroxyl protective group, and
$S^2$ and $S^3$ are independently hydroxyl protective groups.

18. A compound of formula:

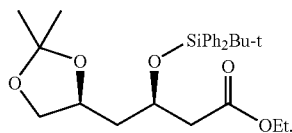

19. A compound of formula:

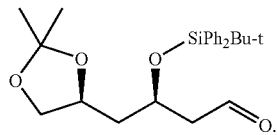

20. A compound of formula:

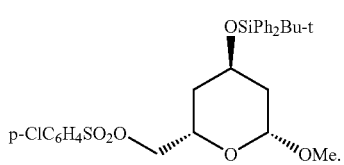

21. A compound of formula:

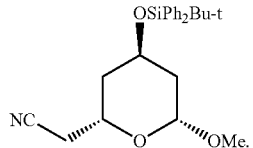

22. A compound of formula:

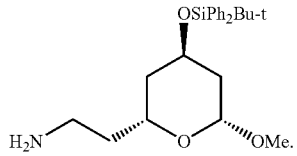

23. A compound of formula:

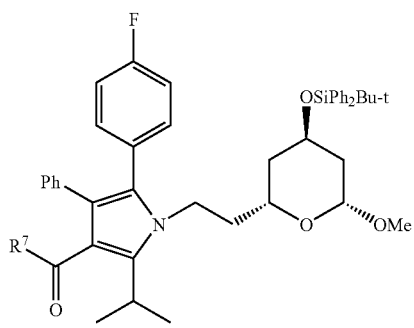

wherein $R^7$ is —$OR^8$, —$NR^9R^{10}$, or halogen, and $R^8$, $R^9$, and $R^{10}$ are independently hydrogen or a straight-chain, branched and/or cyclic, saturated or unsaturated $C_{1-10}$ alkyl group or aryl group, wherein the $C_{1-10}$ alkyl group or aryl group being optionally substituted with 1-3 optionally protected hydroxy- or carboxy groups, 1-3 alkoxy groups, 1-3 alkylamino groups and/or 1-3 halogen atoms, wherein the $C_{1-10}$ alkyl group optionally contains 1-3 oxygen atoms, and/or 1-3 nitrogen atoms and wherein the $C_{1-10}$ alkyl group optionally contains 1 or 2 aryl groups or is substituted by them.

24. The compound according to claim 23, wherein $R^7$ is —O—$C_{1-5}$ alkyl or —NH phenyl.

25. A method for producing a statin using the compound of claim 18 as a starting compound.

* * * * *